United States Patent
Kettler et al.

[11] Patent Number: 6,064,487
[45] Date of Patent: May 16, 2000

[54] METHOD FOR CALCULATING DYE FORMULATIONS OF PIGMENTED EFFECT DYEING TONES

[75] Inventors: Wilhelm H. Kettler; Matthias Kolb, both of Wuppertal; Hartmut Krause, Wermelskirchen, all of Germany

[73] Assignee: Herberts GmbH, Wuppertal, Germany

[21] Appl. No.: 09/214,441

[22] PCT Filed: May 17, 1998

[86] PCT No.: PCT/EP98/02699

§ 371 Date: Jan. 11, 1999

§ 102(e) Date: Jan. 11, 1999

[87] PCT Pub. No.: WO98/53285

PCT Pub. Date: Nov. 26, 1998

[30] Foreign Application Priority Data

May 17, 1997 [DE] Germany ............... 197 20 887

[51] Int. Cl.[7] .................................................. G01J 3/50
[52] U.S. Cl. ................................. 356/402; 250/226
[58] Field of Search .......................... 356/402, 405, 356/406, 407, 425; 250/226

[56] References Cited

U.S. PATENT DOCUMENTS

| | | | |
|---|---|---|---|
| 3,690,771 | 9/1972 | Armstrong, Jr. et al. | 250/226 |
| 3,916,168 | 10/1975 | McCarty et al. | |
| 4,479,718 | 10/1984 | Alman | 356/405 |
| 4,711,580 | 12/1987 | Venable | 356/406 |
| 5,231,472 | 7/1993 | Marcus et al. | 356/402 |

FOREIGN PATENT DOCUMENTS

2 293 448  3/1996  United Kingdom.

*Primary Examiner*—F. L. Evans
*Attorney, Agent, or Firm*—Pillsbury Madison & Sutro LLP

[57] ABSTRACT

Process for calculating colour formulations of pigmented special-effect shades wherein i) for each pigment on which a colorant system is based a set of calibration panels is created, and the associated reflection factors are determined experimentally, ii) from the measured reflection factors for each pigment on which the colorant system is based, the optical material parameters are determined using a radiation transport model to describe the diffusion of light in particulate media, iii) from all the platelet-like special-effect pigments on which the colorant system is based and in each case a fixed quantity of one or more colouristically inert topology-influencing fillers, so-called pseudopigments are formed whose optical material parameters are likewise determined by way of a calibration scale, iv) and, the formulation components and pigments and/or associated pseudopigments from a colorant system being specified, the reflection spectra of a special-effect shade which is to be rematched are simulated mathematically by reference to the optical material parameters, using a suitable radiation transport model to describe the diffusion of light in particulate media, with the associated quantity resulting in respect of each pigment, each pseudopigment and the topology-influencing filler.

4 Claims, 5 Drawing Sheets

METHOD FOR CALCULATING DYE FORMULATIONS OF PIGMENTED EFFECT DYEING TONES

This application is the national phase of international application PCT/EP98/02699 filed May 8, 1998 which designated the U.S.

FIELD OF THE INVENTION

The invention relates to a process for calculating colour formulations of special-effect shades which may be pigmented. The process has applications in the field of special-effect-imparting surface coating, in particular when all the pigments with which a surface coating is coloured must be determined in order to rematch shades to a shade pattern. The process can, however, also be employed for calculating colour formulation corrections.

BACKGROUND OF THE INVENTION

The rematching of shades of unknown pigmentation is a central problem in all the colouristics areas of a lacquer company. In particular in the automotive coatings sector, there has in recent years been a continuous broadening of the pigment range. Within this, the number of special-effect shades has increased particularly sharply. Stylists increasingly incorporate any combinations of special-effect pigments into shades. In the light of these developments, efficient methods for minimising effort and cost when rematching this class of shade has great economic importance.

Virtually all special-effect pigment types such as, for example, aluminium, interference pigments or liquid crystal pigments are two-dimensional in character, having a lateral extension of the order of 5 to 40 $\mu$m and a thickness of less than 5 $\mu$m. Pronounced brightness and special colour effects can be obtained only when the particles are in optimal parallel alignment relative to the surface of the lacquer. The platelet orientation is a property of the individual lacquer system in which these pigments are used, and is dependent on the application parameters.

When rematching special-effect shades of unknown pigmentation, a range of peripheral conditions must be met in order to guarantee the high quality which is demanded, for example, in the automotive coatings sector. The use of the same pigment types as are used in the colour sample which is to be rematched is a prerequisite for working out a high-quality rematch. Only when the type and particle size distribution of the special-effect pigments used correspond to the components of the colour sample is precise rematching free of metamerism possible at all. Moreover, the topology of the platelet-like special-effect pigments in the applied lacquer is of equal importance, since it is this which ultimately determines the formation and conspicuousness of the brightness and special colour effects.

The rematching of shades of unknown pigmentation in colouristics laboratories today is underpinned by computer-aided methods of calculating colour formulations. Colour formulation calculation is a tool for analysing the pigmentation of shades with the aid of reflection spectroscopy in the visible region of the spectrum and using a suitable radiation transport model to describe the diffusion of light in particulate media and thus the reflection spectra which are detectable metrologically.

Figure 2A:
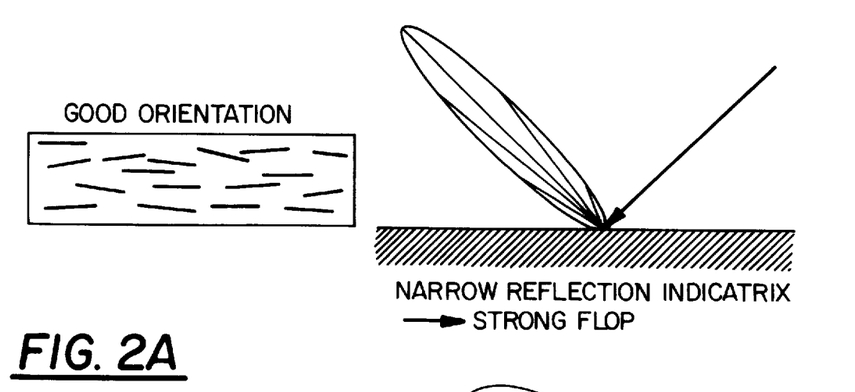
FIGS. 2A and 2B show the qualitative influence of particle topology on the reflection indicatrix of special-effect shades, using the example of a system having lamellar aluminium pigments as the special-effect-imparting agent.
Figure 2B:
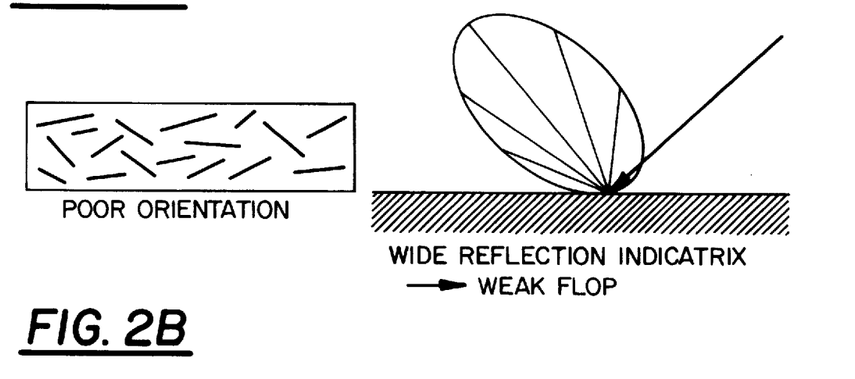
Figure 2C:
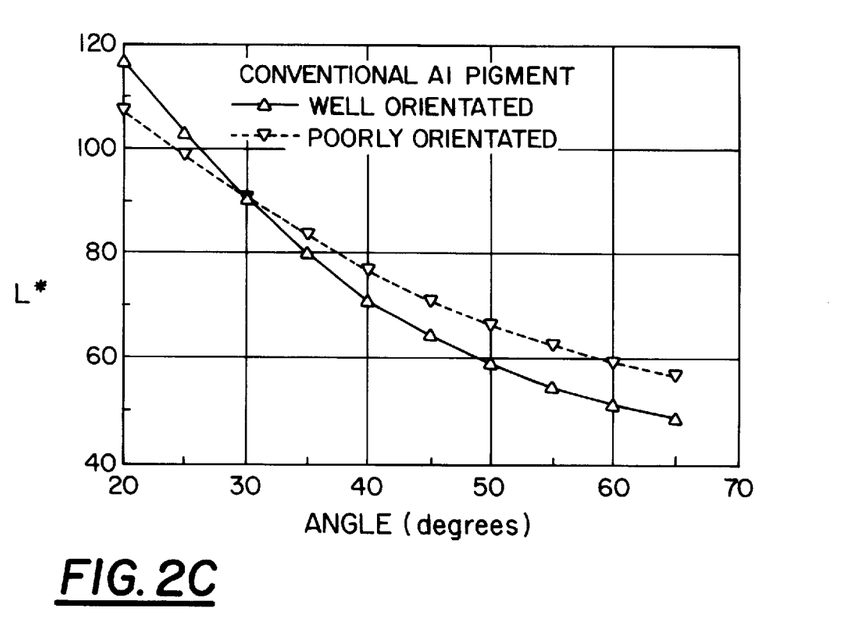
FIG. 2C, the angular dependence of the brightness (L*) of an aluminium mass tone is represented in respect of both undisrupted (Δ) and disrupted (▽) particle topology.

The quality of the calculated formulations is dependent on standardisation of all the components in a mixed lacquer system and on constancy of the application parameters. Any deviations in the pigment topology of the current shade pattern from the pigment topology of the binder system used for the rematch necessarily lead to simulation results of a lower quality (FIGS. 2A to 2C). If the special-effect pigments are orientated differently in the colour sample which is to be rematched and the binder system used for working out the rematch, there are two possibilities: (i) the horizontal alignment of the platelet-like pigment particles in one's own binder system is less good, and (ii) the orientation in one's own binder system is better, than that in the shade which is to be rematched.

In the former case it is not possible using one's own binder system to achieve a precise rematching of the shade to be processed. If orientation of the particles in one's own lacquer system is better, their topology can be disrupted by the addition of colouristically inert fillers/pigments of suitable particle size distribution which are matched to the topology present in the colour sample which is to be rematched. Since, however, these fillers/pigments are without colouristic effect because their refractive index is comparable with the embedding medium, they cannot be treated like a pigment within the context of colorant calibration and included in the colour formulation calculation. In the conventional colour formulation calculation of special-effect shades, therefore, no account can be taken of topology as an influencing factor.

SUMMARY OF THE INVENTION

The object of the invention was to provide a process for calculating colour formulations of special-effect shades, which takes account quantitatively of the influence of the particle topology of special-effect pigments, thus increasing the accuracy of the colour formulation calculation and substantially reducing the number of tinting steps necessary to work out a colour formulation.

The object is achieved by a process for calculating colour formulations of special-effect shades, which is characterised in that i) for each pigment on which a colorant system is based a set of calibration panels is created, and the associated reflection factors are determined experimentally, ii) from the measured reflection factors for each pigment on which the colorant system is based, the optical material parameters are determined using a radiation transport model to describe the diffusion of light in particulate media, iii) from all the platelet-like special-effect pigments on which the colorant system is based and in each case a fixed quantity of one or more colouristically inert topology-influencing fillers, so-called pseudopigments are formed whose optical material parameters are likewise determined by way of a set of calibration panels, iv) and, the formulation components and pigments and/or associated pseudopigments from a colorant system being specified, the reflection spectra of a special-effect shade which is to be rematched are simulated mathematically by reference to the optical material parameters, using a suitable radiation transport model to describe the diffusion of light in particulate media, with the associated quantity resulting in respect of each pigment, each pseudopigment and the topology-influencing filler.

Colorant systems should be understood to mean any systems of absorption pigments and/or special-effect pigments. The number and choice of pigment components are not subject to restrictions here. They may be adapted in any manner to the relevant requirements. For example, such a colorant system can be based on all the pigment components of a standardised lacquer mixing system.

Colouristically inert fillers are understood to mean any substances/compounds which, on the one hand, are without colouristic effect, that is to say which exhibit a very low self-absorption and whereof the refractive index is the same as the refractive index of the embedding medium, and which, on the other hand, are able to influence the orientation (parallel alignment) of the special-effect pigments in the surface coating, that is to say in the applied lacquer film. Inert substances/compounds which may, for example, be used are indicated hereinbelow, without the concept of colouristically inert, topology-influencing fillers being, however, restricted to these examples. Suitable inert fillers corresponding to the definition may, for example, be transparent or semi-transparent fillers or pigments such as, for example, barium sulfate, magnesium silicate, aluminium silicate, crystalline silicon dioxide, amorphous silica, aluminium oxide, microbeads or micro-balloons of, for example, glass, ceramic or polymers of, for example, from 0.1–50 $\mu$m in size. Furthermore, any solid inert organic particles such as, for example, urea-formaldehyde condensation products, micronised polyolefine wax and micronised amide wax can be used as inert fillers. The inert filers may in each case also be used in mixture. Preferably, however, only one filler is used.

Special-effect pigments are understood to mean any pigments which exhibit a platelet-like structure and impart special decorative colour effects to a surface coating. For example, special-effect pigments are any special-effect-imparting pigments which are conventionally usable in automotive and industrial coating. Examples of such special-effect pigments are pure metal pigments such as, for example, aluminium, iron or copper pigments, interference pigments such as, for example, titanium dioxide-coated mica, iron oxide-coated mica, mixed oxide-coated mica (for example coated with titanium dioxide and $Fe_2O_3$ or titanium dioxide and $Cr_2O_3$), metal oxide-coated aluminium, or liquid crystal pigments.

The process according to the invention for calculating colour formulations is applicable to any combinations of special-effect pigments and to any combinations of different special-effect pigments with colour-imparting absorption pigments.

The absorption pigments are, for example, conventional organic or inorganic absorption pigments which are usable in the lacquers industry. Examples of organic absorption pigments are azo, phthalocyanine, quinacridone and pyrrolopyrrole pigments. Examples of inorganic absorption pigments are iron oxide pigments, titanium dioxide and carbon black.

An indispensable precondition for the process according to the invention for calculating colour formulations is knowledge of the optical material parameters of all the mixed lacquers and pigments which build a mixed system. In order to describe the reflection indicatrix of special-effect shades, a radiation transport model must be selected with which the angular dependence of the reflection factor can be described with sufficient accuracy.

A possible formulation is, for example, the azimuth-independent form of the radiation transport equation $$\mu \frac{d\,I(x,\mu)}{dx} = -(\kappa+\sigma)I(x,\mu) - \frac{\sigma}{2}\int_{-1}^{1} p(\mu,\mu')I(x,\mu')d\mu' + \frac{\sigma}{4\pi}I_o p(\mu,-\mu_o)e^{-(\kappa+\sigma)x'/\mu_o}$$

This model couples macroscopically measurable variables such as reflection with pigment-optical material parameters such as the absorption ($\kappa$) and scattering ($\sigma$) coefficients and the phase function ($p(\mu,\mu')$).

However, any more generally valid theoretical model can also be used to describe the radiation diffusion in pigmented media.

The azimuth-independent radiation transport equation couples the intensity $I(x,\mu)$ of the radiation at the geometric depth x with the optical material parameters of the pigments. In addition to the absorption ($\kappa$) and scattering ($\sigma$) coefficients, the phase function $p(\mu,\mu')$, which describes the angular dependence of light scattering at the individual pigment particles, must also be determined, where $\mu$=cos $\theta$($\theta$=scattering angle). In the case of mixtures, all the optical material parameters (scattering coefficient, absorption coefficient, phase function) are composed from the sum of the individual contributions, weighted by the respective pigment concentration. The optical material parameters are determined experimentally from the reflection factors by way of a set of calibration panels. If these material variables are known, the reflection behaviour of opaque or transparent lacquers pigmented in any manner can be calculated quantitatively for each measuring geometry with the aid of the radiation transport equation.

The optical material parameters describe the properties of the pigments as they are present in dispersed form in the respective binder system. They are wavelength-dependent and must be determined in respect of each desired wavelength. In the simplest case, a specific set of calibration panels is prepared in respect of each pigment, and the reflection factor or radiation density factor is measured in the region of the spectrum which is of interest, at different illumination and observation geometries. For example, calibration panels can be made for this purpose with the full colour of the pigment and with blends of the pure pigment with black or white, in the case of opaque coatings or transparent coatings of a pigment over two different substrates of known reflection such as, for example, white and black.

Since the topology of the platelet-like special-effect pigments in the lacquer film is also involved in determining the angular dependence, only shades whose pigment topology is comparable can be worked out mathematically using the optical calibration data stock generated for a mixed system. If a better alignment of the special-effect pigments is present in the shade which is to be rematched than in the mixing system, this shade is rematchable only conditionally and with some loss of quality. If, on the other hand, the horizontal alignment of the special-effect pigments in the shade which is to be rematched is less good than in the mixing system, the spatial arrangement of the special-effect pigments in the mixing system can be adapted with topology-influencing but colouristically inert fillers of suitable particle size distribution. Since these fillers have no particulate character within the meaning of radiation transport theory, because their refractive index is comparable to the embedding medium, no optical material parameters can be determined in their case as they can in the case of the pigments.

According to the invention, so-called pseudopigments are therefore formed in the present process for calculating colour formulations, by mixing each of the platelet-like special-effect pigments with a fixed quantity of one or more topology-influencing but otherwise colouristically inert fillers (see definition hereinabove). The optical material parameters of the pseudopigments are then determined by way of a set of calibration panels in a procedure analogous to that applied to the other pigments contained in a colorant system.

The pseudopigments are considerably disrupted in their topology by comparison with the pure special-effect pigments. In calculating the colour formulation, continuous interpolation between the topologies of the two pigments can take place by mixing the topologically undisrupted special-effect pigment with the topologically disrupted pseudopigment. Simultaneously, in addition to the associated quantity in respect of each pigment, the formulation calculation provides the quantity of the topology-influencing filler to be added.

Moreover, by taking into account in the simulation the disturbance of the flop behaviour of the pigment platelets, one can ensure that all the required coloured components (absorption pigments) can also be calculated into a formulation. Without disturbance of the special effect, a phenomenon frequently occurs when calculating the colour formulation, whereby coloured components which are actually required register as zero concentration in the simulation because they adversely affect the target variable of the iteration (sum of the weighted squared residuals). This adverse effect on the result is to be expected here only because the special-effect-imparting component orientates itself too well by comparison with the shade which is to be rematched, causing wide deviations between the measured and the calculated reflection indicatrix (FIGS. 2A to 2C).

In this procedure the maximum available quantity of inert filler is dependent on the quantity of filler used when creating the calibration panels to determine the optical material parameters for the pseudopigments. This constituent of the blend should be selected such that in the result sufficiently accurate interpolation is possible between undisrupted and disrupted pigment variants, and a sufficient quantity of inert filler can be calculated into formulations. This can only be verified experimentally.

Figure 1A:
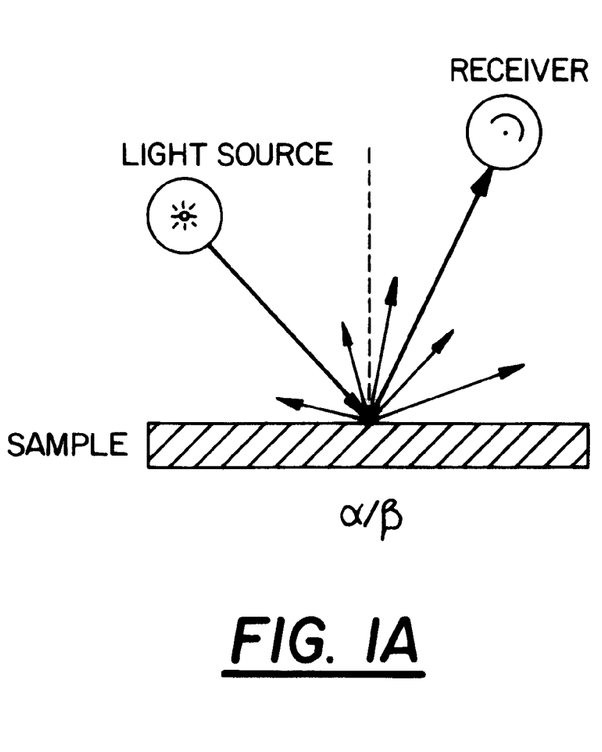
In FIG. 1A, systems with observation modulation are shown, and in FIG. 1B, systems with illumination modulation are shown. The measurement angle $|\epsilon|$ is relative to the gloss angle here. If the light source and the receiver are located on the same side of the gloss angle, the measurement angle has a positive sign. If the light source and the receiver are located on different sides of the gloss angle, the measurement angle is given a negative sign.
Figure 1B:
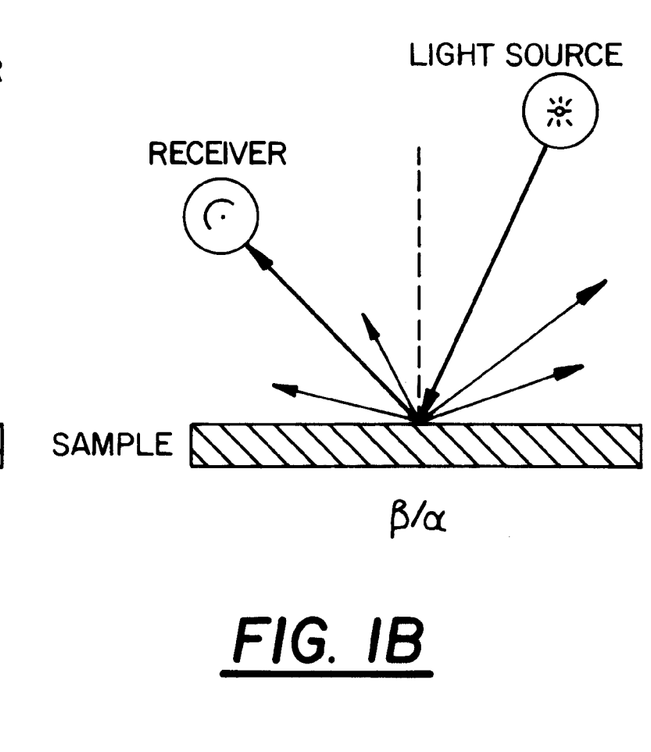

A goniospectrophotometer is conventionally used in order to characterise instrumentally the optical properties of coloured surface coatings however they may be pigmented, that is to say, in order to detect the reflection factors metrologically. A stationary or portable goniospectrophotometer having symmetrical (for example 0°/α or α/0°) or asymmetrical (for example 45°/α or α/45°) measuring geometry can be used. The range of angle of observation to be covered is dictated by the approximation which is respectively used for the radiation transport equation. Both equipment with illumination modulation and equipment with observation modulation can be used (see FIGS. 1A to 1B). In the case of symmetrical measuring geometry, illumination (observation) is perpendicular to the sample surface, and observation (illumination) is at different polar angles θ ($0° < θ < 90°$). The aperture of the illumination and observation optical system selected here should not be too large. Alternatively, when an asymmetrical measuring geometry is used, illumination (observation) can be at a polar angle of 45°, and for the observation a plurality of angles $\epsilon$ may be selected from the range $0° < \epsilon < 90°$, for example, where $\epsilon$ is understood to be the angular difference from the gloss angle (see FIGS. 1A to 1B).

The material parameters are then determined by adapting the radiation transport equation or a more generally valid model within the meaning of the $L_2$ norm to these experimental data, as described hereinabove.

The process described is implementable, while not being obligatory, for any tools of computer-aided pigmentation analysis based on reflection spectroscopy such as calculating combination formulations and calculating correction formulations. In the former case all the combinations of m constituents of an n-component mixing system, which are specified by the user are calculated-through automatically and are sorted according to a user-defined criterion (such as, for example, colour difference, metamerism index or weighted sum of squared residuals). Here account is taken of the topology in the same way as in interactive working-out of formulations, in which the user selects the pigments to be used for a formulation. The total number of all formulations which can be differentiated can be calculated by the formulaic correlation:

$$C_m^n = \binom{n}{m} = \frac{n!}{m!(n-m)!}$$

Since, for a variety of reasons, the formulation when mixed generally still exhibits a visually and instrumentally detectable colour difference from the target shade, a facility for correcting formulations with the aim of reducing deviations would be a desirable aid to the colourist. For this reason, various methods have been developed for the case of plain shades, and all are translatable to the field of special-effect shades. The described method for taking account of the topology of special-effect pigments can also be applied without further modification to the calculation of correction formulations—independently of the type of method chosen (for example the method of correction factors), because for correcting formulations also, it is again necessary to use the algorithm of colour formulation calculation.

The improvement in the process according to the invention for calculating colour formulations as compared with conventional methods resides in the use of the comprehensive optical material parameters of the pigments, which must be determined from a set of calibration panels with the aid of the radiation transport equation, with account being taken quantitatively of the influence of particle topology.

BRIEF DESCRIPTION OF THE DRAWINGS

The invention is explained in more detail below by reference to the Example and Drawings, which show:

FIGS. 1A to 1B: comparison of measurement geometries used in goniospectrophotometers.

FIGS. 2A to 2C.

FIGS. 4A and 4B: Experimentally measured and calculated reflection spectra for the beige special-effect shade are represented. FIG. 4A shows undisrupted and FIG. 4B shows disrupted (right) particle topology. The angle of observation is the parameter of the family of curves. For the sake of greater clarity, the spectra of only some angles are shown. In both cases the measured spectra are represented by a solid line and the calculated spectra by a dotted line.

STD—standard
OIF—no inert filler
MIF—with inert filler

DETAILED DESCRIPTION OF THE INVENTION

The process according to the invention for calculating colour formulations will be demonstrated on the rematching of a special-effect shade typical of the automotive sector. A shade pattern with a beige special-effect shade (Toyota Beige Metallic) is present, to which a correspondingly worked-out formulation should lead.

Figure 3:
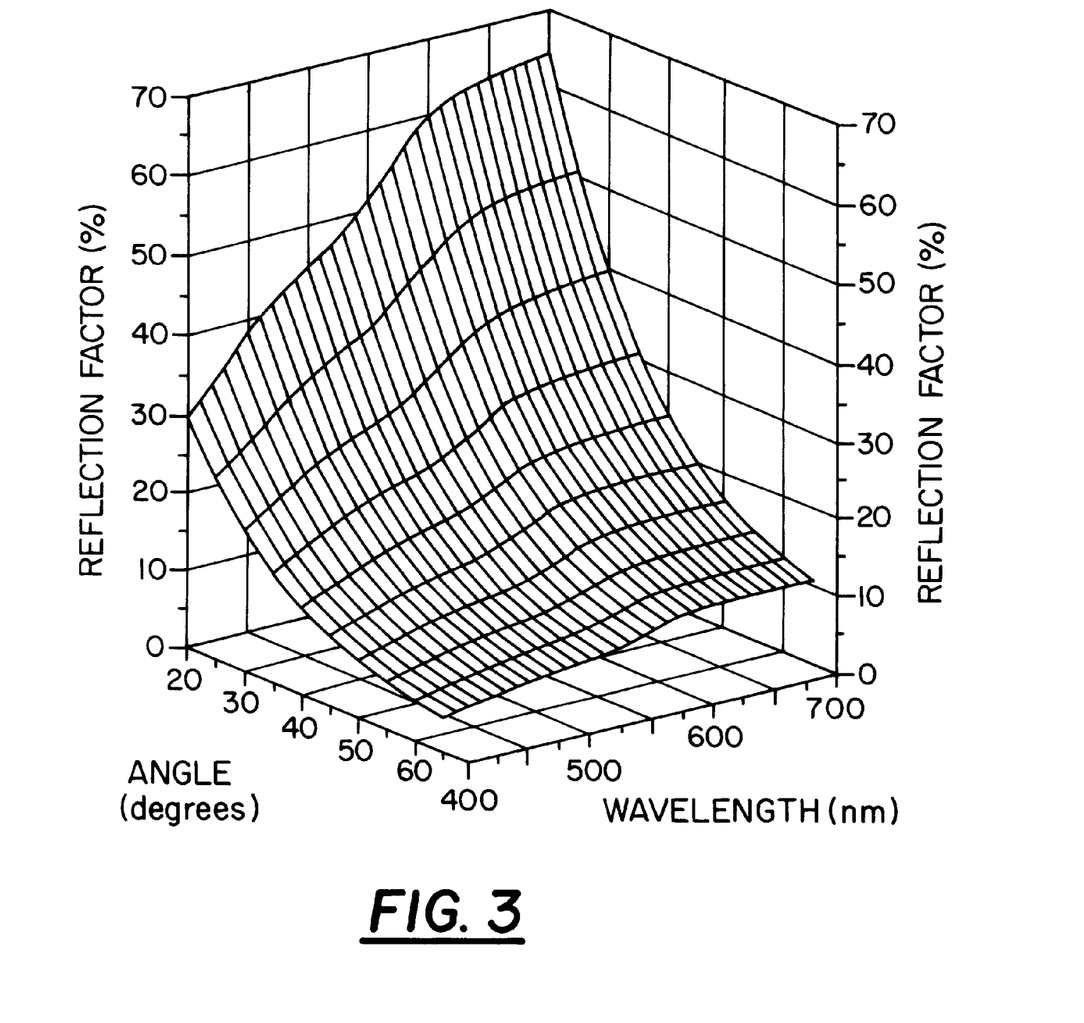
FIG. 3: Experimentally measured reflective surface of a beige special-effect shade in the visible region of the spectrum (400 nm $\leq \lambda \leq$ 700 nm) and within a detected angle range of $20° \leq \epsilon \leq 65°$). This shade can be rematched by combining a brilliant aluminium pigment with a yellow pigment and a black pigment.
Figure 4A:
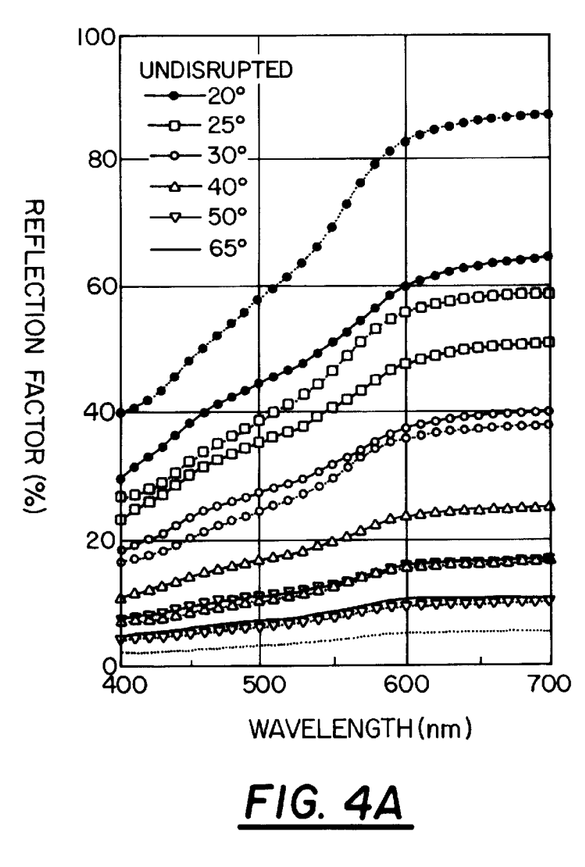
Figure 4B:
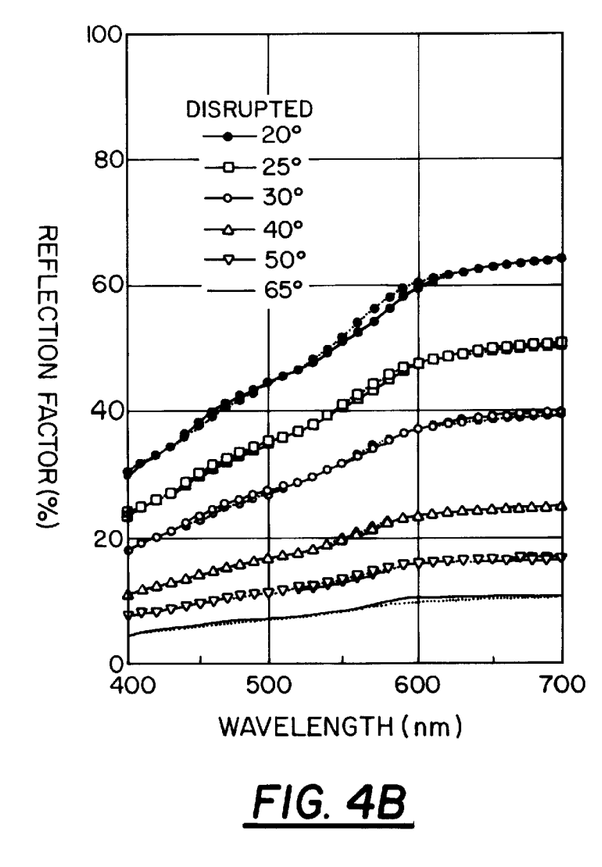
Figure 5A:
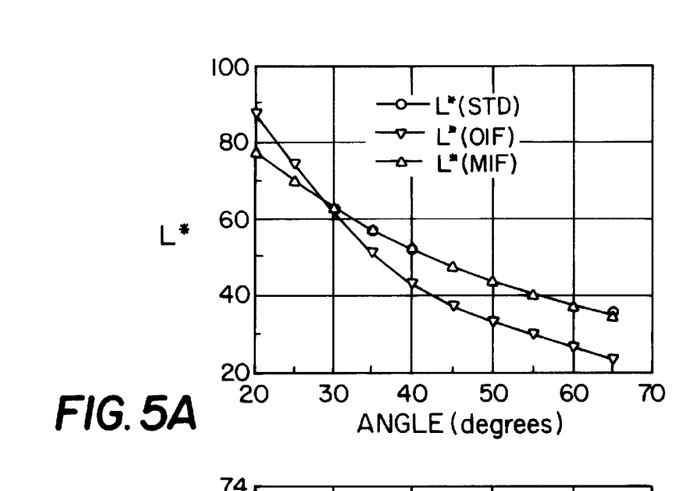
FIGS. 5A, 5B, 5C and 5D: Angular dependence of the colorimetric measured values in respect of the beige special-effect shade represented in FIG. 3, and of the calculated colour formulations for the cases of undisrupted and disrupted particle topology.
Figure 5B:
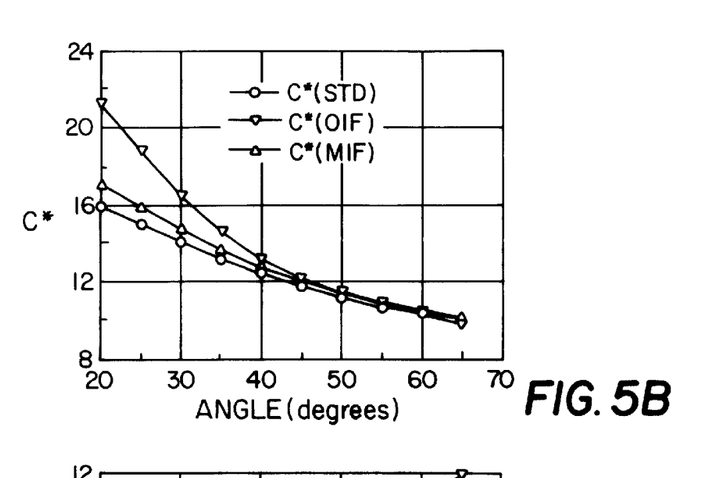
Figure 5C:
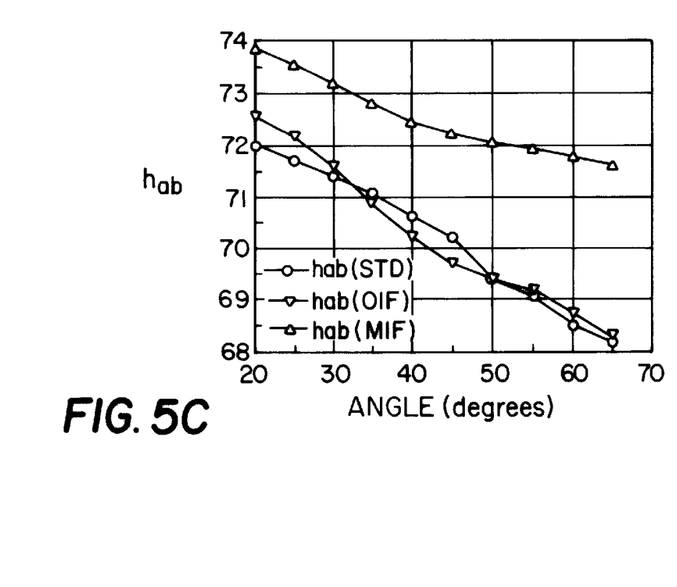
Figure 5D:
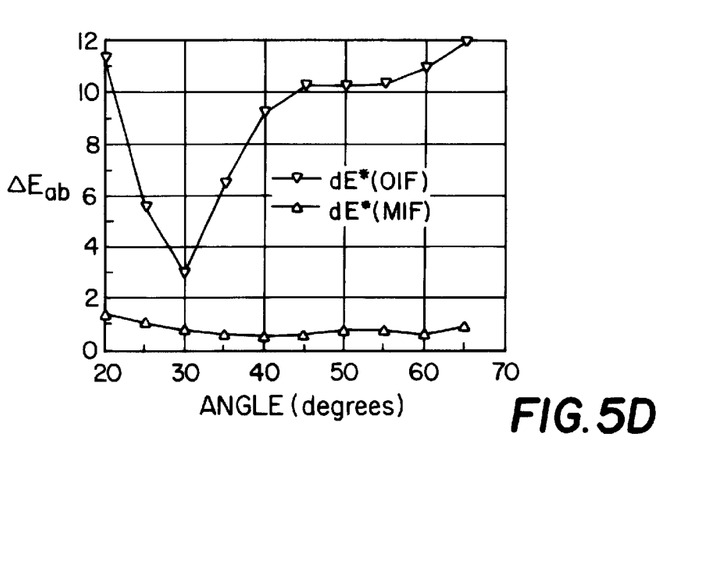

The shade pattern is first measured using a goniospectrophotometer. FIG. 3 shows the reflectance surface measured for the wavelength range 400 nm $\leq \lambda \leq$ 700 nm and the angle range 20° $\leq \epsilon \leq$ 65° for the case of perpendicular incident radiation. As can be seen from FIG. 3, this beige special-effect shade exhibits a marked angular variation. A brilliant aluminium pigment having a pronounced angular variation has been used here as the special-effect-imparting component. A yellow absorption pigment and carbon black are specified additionally for the rematch. The reflectance surface can now be simulated by reference to the optical material parameters of the pigments specified. In the simulation of the reflectance surface, however, it becomes apparent (see FIG. 4A) that the aluminium pigment is better orientated in the lacquer system used than in the colour sample which is to be rematched. As a result the rematch is too light in the region near the gloss angle and too dark in the region remote from the gloss angle. This case is favourable, because the special effect in one's own binder system must be disturbed in order to obtain the reflection properties of the reference shade. This discrepancy can be eliminated virtually completely by taking account of the disrupted pseudocomponent associated with the specified aluminium pigment. It can be seen from FIG. 4B, that there is now very good agreement between the reflectance surfaces of the hade pattern and those of the simulation. This marked improvement in the simulation result is also reflected in the calorimetric data of both calculated formulations, which are set out in FIGS. 5A, 5B, 5C and 5D. Without disrupting the particle topology, the average colour difference from the first formulation when mixed is around $<\Delta E^*_{ab}> \approx 8.9$ CIELAB units, which can be reduced considerably by incorporating the topology-disrupted variant into the calculation $<\Delta E^*_{ab}> \approx 0.8$. In the latter case, the existing hue angle difference in respect of coloured tone necessitates only a post-adjustment of the coloured component (yellow) of the formulation. The mathematical calorimetric results correspond to those of the relevant formula when mixed.

The Table which follows sets out the calculated formulation results (the concentration of all components which has been determined) for the beige special-effect shade (shade pattern) for the case of undisrupted pigment topology and for the case of disrupted pigment topology. Both formulations contain as the pigment constituents aluminium pigments, yellow pigments and carbon black. The filler which influences the orientation of the aluminium pigment is an additional component in the case of the topology-sensitive formulation ($C_{disrupted}$)

|  | $C_{undisrupted}$ (%) | $C_{disrupted}$ (%) |
|---|---|---|
| Aluminium pigment | 66.21 | 60.00 |
| Yellow pigment | 19.16 | 15.21 |
| Carbon black | 14.64 | 16.59 |
| Filler | — | 8.21 |

We claim:

1. A process for calculating a colour formulation of a pigmented special-effect shade, characterised in that i) for each pigment on which a colorant system is based a set of calibration panels is created, and the associated reflection factors are determined experimentally, ii) from the measured reflection factors for each pigment on which the colorant system is based, optical material parameters are determined using a radiation transport model to describe the diffusion of light in particulate media, iii) from all the platelet special-effect pigments on which the colorant system is based and in each case a fixed quantity of one or more colouristically inert topology-influencing fillers, pseudopigments are formed whose optical material parameters are likewise determined by way of calibration panels, iv) and, the formulation components and pigments and/or associated pseudopigments from a colorant system being specified, the reflection spectra of a special-effect shade which is to be rematched are simulated mathematically by reference to the optical material parameters, using a suitable radiation transport model to describe the diffusion of light in particulate media, with the associated quantity resulting in respect of each pigment, each pseudopigment and the topology-influencing filler.

2. A process for calculating a colour formulation of a pigmented special-effect shade according to claim 1, characterised in that the radiation transport model is the azimuth-independent form of a radiation transport equation.

3. A process for calculating a colour formulation of a pigmented special-effect shade according to claim 1, characterised in that a reflection factor or a beam density factor are determined at different illumination and observation geometries in the spectral region which is of interest, in order to determine the optical material parameters.

4. A process for calculating a colour formulation of a pigmented special-effect shade according to claim 2, characterized in that a reflection factor or a beam density factor are determined at different illumination and observation geometries in the spectral region which is of interest, in order to determine the optical material parameters.

* * * * *

UNITED STATES PATENT AND TRADEMARK OFFICE
CERTIFICATE OF CORRECTION

PATENT NO. : 6,064,487
DATED : May 16, 2000
INVENTOR(S) : KETTLER et al.

It is certified that error appears in the above-indentified patent and that said Letters Patent is hereby corrected as shown below:

On the title page item

[22] PCT Filed: --May 8, 1998--.

Signed and Sealed this

Third Day of April, 2001

Attest:

NICHOLAS P. GODICI

Attesting Officer     Acting Director of the United States Patent and Trademark Office